(12) United States Patent
Kaltenbach et al.

(10) Patent No.: US 6,759,013 B2
(45) Date of Patent: Jul. 6, 2004

(54) MODULAR APPARATUS FOR CHEMICAL MICROANALYSIS

(75) Inventors: Patrick Kaltenbach, Bischweier (DE); Tom A. van de Goor, Foster City, CA (US)

(73) Assignee: Agilent Technologies, Inc., Palo Alto, CA (US)

(*) Notice: Subject to any disclaimer, the term of this patent is extended or adjusted under 35 U.S.C. 154(b) by 0 days.

(21) Appl. No.: 09/156,804

(22) Filed: Sep. 17, 1998

(65) Prior Publication Data

US 2001/0008613 A1 Jul. 19, 2001

(51) Int. Cl.[7] .............. B01L 11/00; B01L 3/02; B01L 3/00; B01L 9/00; G01N 15/06
(52) U.S. Cl. .............. 422/101; 422/68.1; 422/99; 422/100; 422/102; 422/103; 204/193; 204/194; 204/403.01; 204/403.03; 204/409; 204/164; 204/450; 204/451; 436/174; 436/177; 436/178; 436/180
(58) Field of Search .............. 422/68.1, 99, 100, 422/101, 102, 103, 104, 198; 204/193, 194, 403.01, 403.03, 409, 164, 450, 451, 416, 418, 419, 452, 453, 601, 604; 436/174, 177, 178, 180

(56) References Cited

U.S. PATENT DOCUMENTS

| | | | | |
|---|---|---|---|---|
| 3,211,638 A | * | 10/1965 | Halvorsen | 204/195 |
| 4,654,127 A | * | 3/1987 | Baker et al. | 204/1 T |
| 4,806,316 A | * | 2/1989 | Johnson et al. | 422/100 |
| 4,935,040 A | * | 6/1990 | Goedert | 73/23.22 |
| 5,104,512 A | * | 4/1992 | Gombocz et al. | 204/299 R |
| 5,128,104 A | * | 7/1992 | Murphy et al. | 422/102 |
| 5,500,071 A | | 3/1996 | Kaltenbach et al. | 156/272.8 |
| 5,519,635 A | * | 5/1996 | Miyake et al. | 364/497 |
| 5,571,410 A | | 11/1996 | Swedberg et al. | 210/198.2 |
| 5,603,351 A | * | 2/1997 | Cherukuri et al. | 137/597 |
| 5,637,469 A | * | 6/1997 | Wilding et al. | 435/7.21 |
| 5,641,400 A | | 6/1997 | Kaltenbach et al. | 210/198 |
| 5,645,702 A | * | 7/1997 | Witt et al. | 204/501 |
| 5,658,413 A | | 8/1997 | Kaltenbach et al. | 156/272.8 |
| 5,890,745 A | * | 4/1999 | Kovacs | 285/24 |
| 5,906,723 A | * | 5/1999 | Mathies et al. | 204/603 |
| 5,968,331 A | * | 10/1999 | Kambara et al. | 204/450 |
| 5,989,402 A | * | 11/1999 | Chow et al. | 204/601 |
| 6,086,740 A | * | 7/2000 | Kennedy | 204/601 |
| 6,090,251 A | * | 7/2000 | Sundberg et al. | 204/453 |
| 6,100,541 A | * | 8/2000 | Nagle et al. | 250/573 |
| 6,103,199 A | * | 8/2000 | Bjornson et al. | 422/100 |
| 6,143,152 A | * | 11/2000 | Simpson et al. | 204/451 |
| 6,148,508 A | * | 11/2000 | Wolk | 29/825 |
| 6,258,263 B1 | * | 7/2001 | Henderson et al. | 210/198.2 |

FOREIGN PATENT DOCUMENTS

WO WO-9744132 A1 * 11/1997
WO WO00/78454 A1 * 6/2000

OTHER PUBLICATIONS

R. J. Nelson, A. Paulus, A. S. Cohen, A. Guttman, and B. L. Karger, "Use of Peltier Thermoelectric Devices to Control Column Temperature in High–Performance Capillary Electrophoresis", Journal of Chromatography, 480 (1989) 111–127.

* cited by examiner

Primary Examiner—Jill Warden
Assistant Examiner—Brian Sines

(57) ABSTRACT

A modular microchannel apparatus for analysis of an analyte. The apparatus includes a separation unit and a reservoir unit. The separation unit has a microchannel. The analyte can be driven to pass through the microchannel such that the time for the analyte to pass through the microchannel is indicative of the molecular characteristics of the analyte. The reservoir unit has one or more reservoirs for coupling operatively modularly with the separation unit to supply liquid reagents to the separation unit. The reservoirs has prepackaged liquid reagents in it before the reservoir unit is coupled with the separation unit.

15 Claims, 5 Drawing Sheets

MODULAR APPARATUS FOR CHEMICAL MICROANALYSIS

FIELD OF THE INVENTION

The present invention relates to techniques for chemical analysis in a capillary, and more particularly to techniques for chemical analysis in a microchannel requiring interfacing with liquid reservoirs for supplying chemical reagents to the microchannel.

BACKGROUND

In the instrumentation of sample chemical analysis, and especially in separation systems such as gas chromatography (GC), liquid chromatography (LC), and capillary electrophoresis (CE) systems, smaller dimensions will generally result in improved performance characteristics and at the same time result in reduced production cost and analysis cost. In this regard, miniaturized separation systems provide more effective system design, result in lower overhead due to decreased instrumentation sizing, and, additionally, enable increased speed of analysis, decreased sample and solvent consumption and the possibility of increased detection efficiency and probability.

In the design of columnar analytical systems, e.g., LC and GC, the total column volume and total column length are made such that different parts of the analytical system can be connected by the column instead of using transfer lines. Nowadays, in CE, the total column length and total column volume are greatly reduced compared to earlier devices. For the modern CE equipment, connectors become less common but specialty fittings frequently are still needed. The column is still required to have sufficient length to pass from an injector through a temperature-controlled area to the point of detection.

Recently, planar column devices have been developed for chemical analysis. Examples are U.S. Pat. Nos. 5,658,413 (Kaltenbach et al.); 5,645,702 (Witt et al.); 5,641,400 (Kaltenbach et al.); 5,500,071 (Kaltenbach et al.); and 5,571,410 (Swedberg et al.), said patents are incorporated by reference in entirety herein. These devices are quite small, having sizes from a fraction of a centimeter to a few centimeters. In such a device, in addition to a separation compartment (which is a channel), there are usually other compartments for sample handling and preparation before or after the separation step. The advantage of such planar column devices is the ease of integrating different functionality in a single device. However, for such small devices, the total volume is so small that no standard connections can be used to connect these devices to transfer lines. Attempts in using transfer lines for connection will add significantly to the overall volume and therefore adversely affect the separation efficiency. The instrumentation of such small devices presents a challenge. Instead of bringing and connecting a long and relatively large column to different parts of a station, which may have liquid reservoirs, power supply, heating-cooling mechanisms, and other electronic or mechanical parts as in conventional equipment, in making equipment using the planar columns, the instrumentation has to be adapted to interface with the small planar column device. In other words, the various parts of the chemical analysis equipment for instrumentation have to be brought close together in a compact space to interface with such a small device. What is needed is a technique for such compact instrumentation.

SUMMARY

In one aspect, this invention provides modular microchannel apparatuses for the analysis of analyte. In one such apparatus, there is a separation unit and a reservoir unit. When modularly coupled together, the apparatus can be used for chemical analysis. The separation unit includes a microchannel, in which the analyte can be driven to pass through the microchannel according to the molecular characteristics of the analyte. The time for the analyte to pass through the microchannel is indicative of the molecular characteristics of the analyte. The reservoir unit has one or more reservoirs for coupling operatively modularly with the separation unit to supply to it liquid reagents. The reservoirs have prepackaged liquid reagents stored in them before the reservoir unit is coupled with the separation unit.

One advantage of such modular apparatuses is that the individual parts that are to be modularly coupled can be manufactured separately, shipped, and handled separately before assembly for use. Furthermore a wide variety of different parts can be made such that a skilled person can pick and choose among them for the particular application of interest. For example, the skilled person may choose a separation unit with a microchannel of a particular length and size for the analysis of a particular sample and choose a separation unit with a microchannel of a different length and size for a different sample, but choose the same reservoir unit, power unit, heating unit, etc. for the analysis of both samples. Furthermore, the compact design of the modularly coupled apparatus of the present invention greatly reduces the need for connectors and adaptors that traditionally are used to join the analytical columns, detection units, power supply, pressure units, flushing fluid supply, buffer solutions supply, and the like. This compact design allows the analytical operator tremendous flexibility which significantly reduce the burden of carrying a large number of adaptors, connectors, or even whole sets of equipment as in prior technology. The present equipment and technique of analysis can be applied in many chemical and biochemical analyses that are done with traditional analytical techniques using columns, including analyzing chemical, biochemical, and biological samples, including those mentioned in the aforementioned Kaltenbach et al., Witt et al., and Swedberg et al. patents.

BRIEF DESCRIPTION OF THE DRAWINGS

The following figures are included to better illustrate the embodiments of the apparatus and technique of the present invention. In these figures, like numerals represent like features in the several views and the figures are not drawn to scale unless specified to be otherwise.

DETAILED DESCRIPTION OF THE INVENTION

In one aspect of the invention, the present invention provides an apparatus for chemical analysis using small columns, or microcolumns, in which apparatus the various parts can be modularly coupled to function in the chemical analysis. As used herein, the term "modularly coupling" means that the apparatus contains various parts or components which can be assembled for use at the point of use without extensive calibration or testing procedures. In such a design, some of the components may be substituted with some other components to cater to the specific need of analyzing a particular sample. The assembling procedure is typically straight forward and does not require elaborate training or practice.

Modularly Coupled Apparatus

Figure 1:
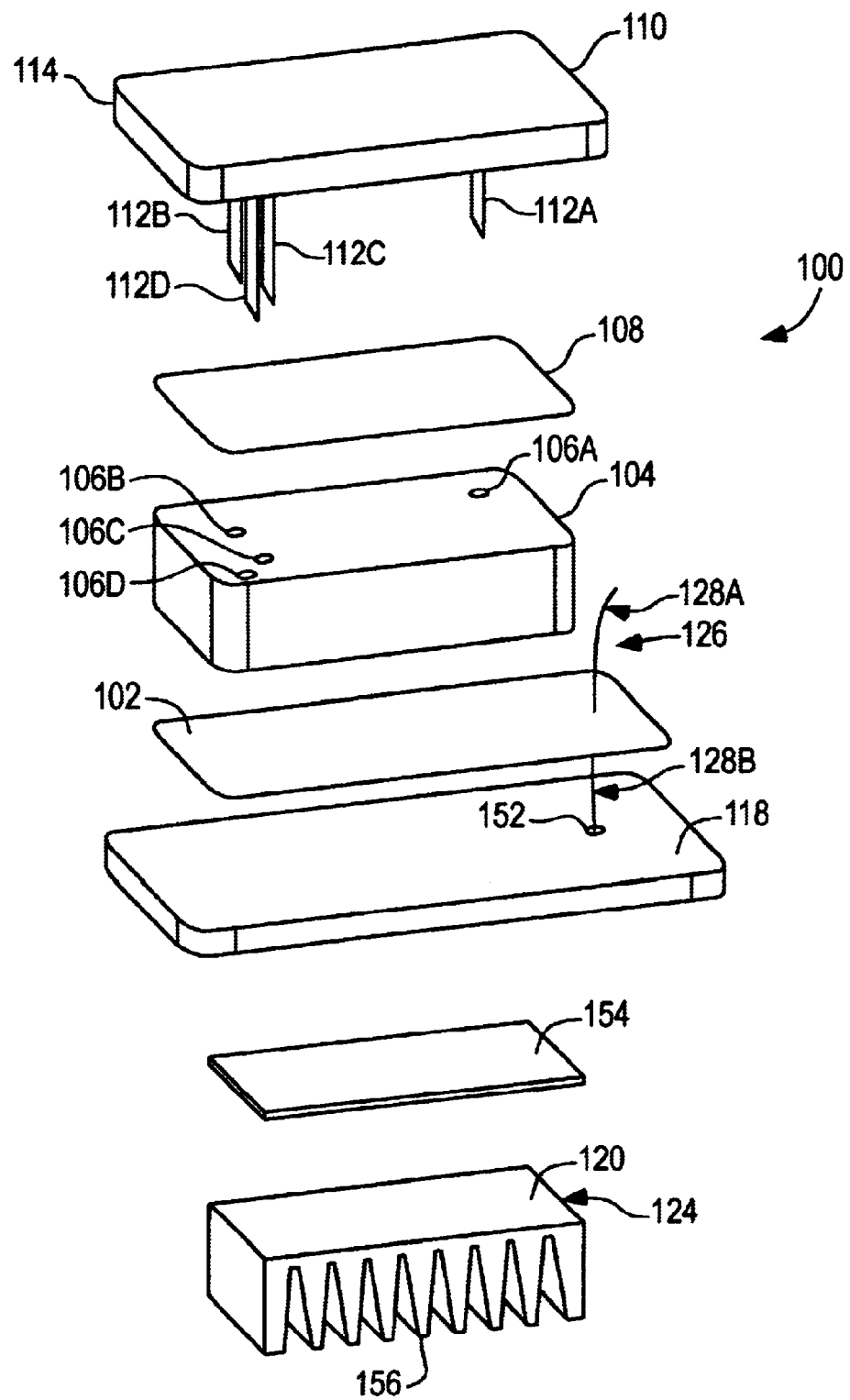
FIG. 1 shows an embodiment of the modularly coupled analytical apparatus of the present invention, in exploded isometric view.
Figure 2:
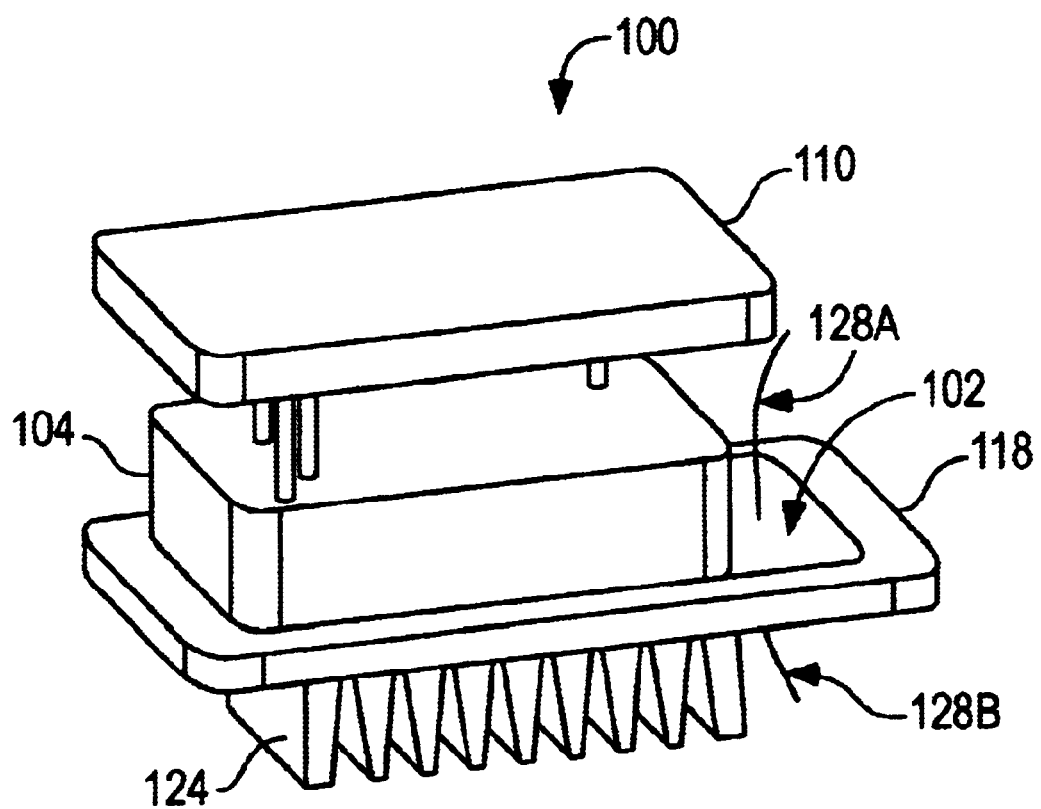
FIG. 2 shows an isometric view of the modularly coupled analytical apparatus of FIG. 1.

FIG. 1 shows an illustrative embodiment of a modularly coupled apparatus of the present invention in exploded isometric view. FIG. 2 shows the same embodiment of the apparatus in assembled form in isometric view. The apparatus 100 includes a chip-shaped separation unit 102 which contains the channel for separation. As used herein, the term "chip-shaped" refers to a shape that is generally rigid, thin, small, and can be manipulated by human fingers. The separation unit 102 will be described in further detail below. On one side (which, for the sake of convenience, is called the "top" side herein) of the separation unit 102 in the apparatus is modularly coupled a block-shaped reservoir unit 104. The reservoir unit 104 has first to fourth reservoirs 106A, 106B, 106C, 106D for supplying liquids to the separation channel in the separation unit 102. On top of the reservoir unit 104 is a membrane (or thin sheet) 108 which covers and seals the top ends of the reservoirs 106A, 106B, 106C, 106D. Although the membrane 108 can be optionally modularly coupled to the reservoir unit 104, it is preferably attached to the reservoir unit 104 to prevent the liquid in the reservoir unit from leaking or spilling. On top of the membrane 108 is modularly coupled a power unit 110 for supplying energy for driving chemicals such as analytes or liquid through the separation channel in the separation unit 102 during chemical analysis. The power unit 110 contains probes 112A, 112B, 112C, 112D that, when the apparatus is assembled, insert through the membrane 108 into the reservoirs 106A, 106B, 106C, 106D respectively for providing energy for driving the chemicals. The probes 112A, 112B, 112C, 112D are attached and supported by base 114 which provides a firm structure for pushing the probes through the membrane 108 into the reservoirs 106A, 106B, 106C, 106D when the apparatus is being modularly assembled.

Modularly coupled to the separation unit 102 on its underside is a support plate 118 for supporting the separation unit 102 such that it can modularly couple firmly with the reservoir unit 104, which in turn operatively couples with the power unit 110, without substantial fluid leakage about the separation unit 102 or the reservoir unit 104. As used herein, the term "operatively couples" or "operatively connects" means two pieces are held in a dimensionally fixed relationship either in direct contact or through one or more interposing pieces between the operatively coupled or operatively connected pieces. Preferably, the support plate 118 is made of a heat conductive material for heat conduction to or from the separation unit 102 for temperature control. Modularly coupled to the support plate 118 is a peltier device 120 for providing heat or cold to the separation unit 102 through the support plate 118. See Nekon et al., "Use of Peltier Thermoelectric Devices to Control Column Temperature in High Performance Capillary Electrophoresis," *J. Chromatogr.* 480, 111–127 (1989).

A heat exchanger 124 is modularly coupled to the underside of the support plate to further provide heat or cold exchange with the separation unit 102 through the support plate 118 and the peltier device 120. A detection device 126 is located close to the separation unit 102 for detection of analyte movement in the separation unit, e.g., at the end of the separation channel in the separation unit 102 to detect the eluting analyte or analytes of interest. An exemplary detection device 126 can contain optical fibers 128A, 128B for providing light to and collecting light from the separation channel. The signal from the detection device 126 can be transferred to a processing unit (not shown in the FIG. 1 or FIG. 2) for analysis of the sample(s) being processed in the apparatus 100. It is to be understood that this optical fiber detector is described for illustrative purposes and other detection techniques using fluorescence, or conductivity can be used. Such alternative detection techniques are known in the art.

Figure 3:
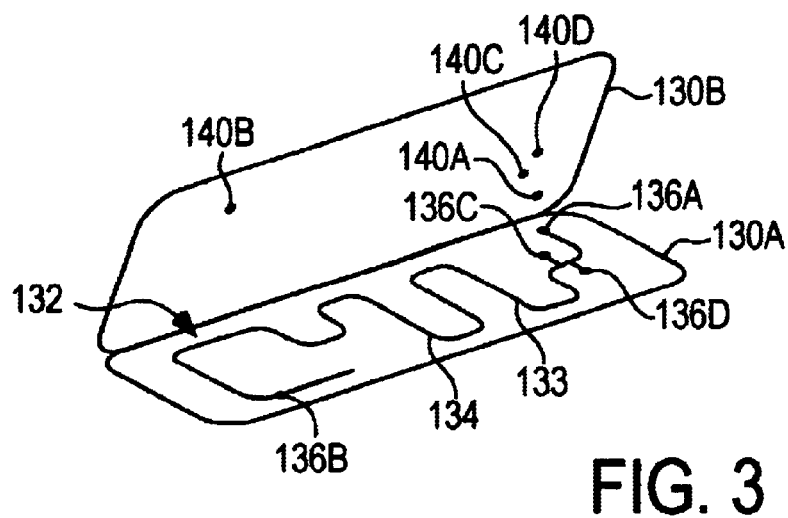
FIG. 3 shows an isometric view an embodiment of the separation unit according to the present invention.

The chip-shaped separation unit 102 is shown in FIG. 3 in further detail. It is to be understood that the planar column device of FIG. 3 is showed merely for illustration and is not meant to be limiting, since many variations of planar column devices are known in the art. Although, for ease of fabrication, the separation unit 102 is chip-shaped, it can be made in any dimensional shape (for example, block-shaped) with which modular coupling can be done with other components.

In FIG. 3, the separation unit 102 is made by joining two plate-like halves together. A first plate half 130A includes a microchannel 132, which is the channel for separation of analytes. The microchannel 132 may have loops 134 to provide adequate length for analysis in a small compact size for the separation unit 102. A input end 136A and an output end 136B of the microchannel 134 provides an entrance and exit for liquid and samples. Additionally, ports 136C, 136D provide access for input or output of liquid or reagents.

Figure 4:
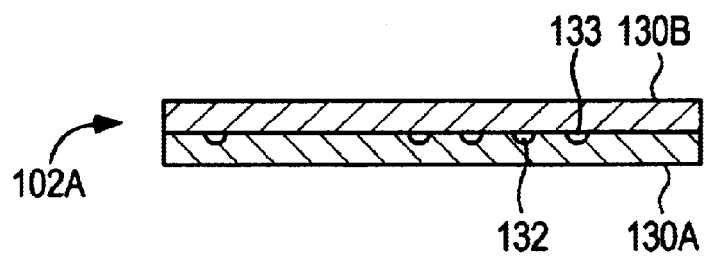
FIG. 4 shows a sectional view of an embodiment of a separation unit according to the present invention.

As used herein, the term "halves" when referred to plate-like parts of the separation unit, may, but not necessarily be mirror images of other halves associated therewith. In the embodiment shown in FIG. 3 and FIG. 4, the first half 130A contains a channel 133 which will form a microchannel 132 when the two halves 13aA and 130B are coupled together. In this embodiment, the second half 130B is just a cover plate and contains no channel. The channel on the surface of the first half 130A is open along its length. It is only when covered by the cover plate second half 130B that the open channel becomes closed along its length, forming the microchannel 132. The cover plate second half 130B has apertures 140A, 140B, 140C, 140D to provide access for liquid to ports 136A, 136B, 136C, 136D to the microchannel 132. Although not shown in the figure, there can also be depressions in either or both of the halves 130A, 130B for forming chambers for reaction, storage, etc. FIG. 4 shows a cross-sectional view of the separation plate 102A.

Figure 5:
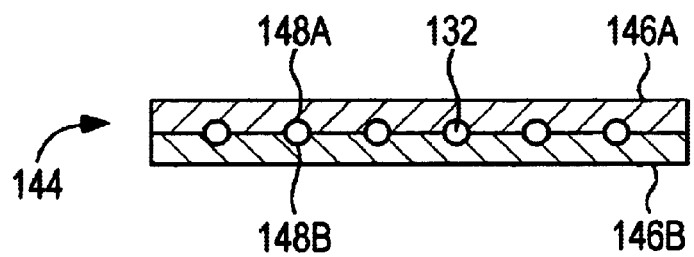
FIG. 5 shows a sectional view of the embodiment of the separation unit of FIG. 3.
Figure 6:
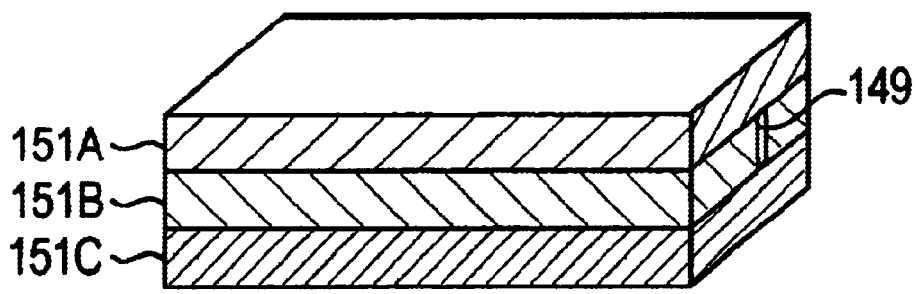
FIG. 6 shows an isometric view of a section of an embodiment of a separation unit made from more than two layers of substrates according to the present invention.

In another embodiment, the second half (i.e., in the position of the cover plate) can also contain a microchannel in addition to the microchannel in the first half (or first plate), e.g., first half 130A. One possibility in such a design is having the microchannel in the second half being a mirror image of the first half. Thus, when the two halves are joined together, the separation unit will have a microchannel that is symmetrical in cross section. Such an embodiment is shown in FIG. 5. In FIG. 5, the separation unit 144 includes a first half 146A having a microchannel 148A and a second half 146B having a microchannel 148B. In yet another embodiment, the separation unit can be made with more than two "halves" or pieces. For example, the separation unit can have three, four, or even more pieces joined together, as shown, for example, in FIG. 6. The pieces (or layers of substrates) 151A, 151B, 151C are made such that the microchannel 132 passes from being between pieces 151A and 151B to being between pieces 151B and 151C by means of a through hole 149 that passes through the piece 151B to join the microchannel on the upper side and the microchannel on the lower side of the piece 151B. As used herein, the term "substrate" refers to a piece of material from which a "half" of a separation unit is made. Separation units of such multilayer structures allows substantial increase in microchannel length without increasing the width and length of the separation unit.

Figure 7A:
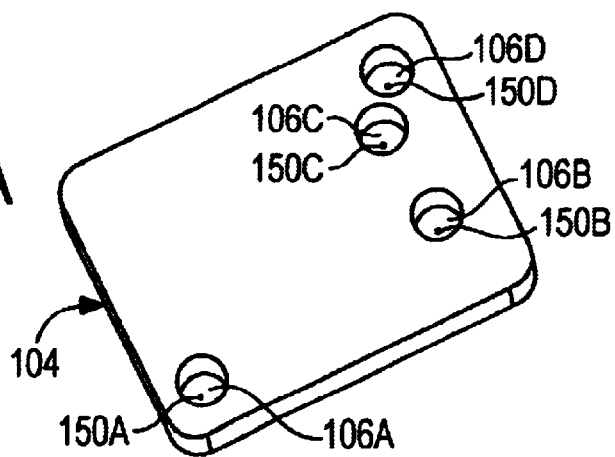
FIG. 7A shows an isometric view of an embodiment of an reservoir unit according to the present invention.

FIG. 7A shows an embodiment of a reservoir unit of the present invention. The reservoir unit 104 is a plate with adequate thickness to include reservoirs 106A, 106B, 106C, 106D for containing sufficient liquid for the analysis to be performed. The reservoirs each can also be made to have larger width, length, or diameter, depending on the shapes thereof, such that the reservoir unit 104 can be thin. Preferably, although not necessarily, at the bottom of the reservoirs 106A, 106B, 106C, 106D are holes 150A, 150B, 150C, 150D to provide liquid passage to the apertures 140A, 140B, 140C, 140D in the second half 130B that lead to the separation microchannel 132 when the separation unit 102 and the reservoir unit 104 are modularly coupled together. Instead of such apertures, bigger openings can be used. Preferably, before modular coupling, the underside (the side that faces the separation unit 102) of the reservoir unit 104 is covered by a cover sheet (or membrane), which is not shown in the figure. The cover sheet prevents liquid from escaping from the holes 150A, 150B, 150C, 150D before modular coupling. The reservoir unit 104 is prepackaged with appropriate liquids in the reservoirs 106A, 106B, 106C, 106D so that the reservoirs units can be shipped and moved around conveniently before modular coupling. Just prior to coupling with a separation unit, the cover sheet is peeled off to open the holes 150A, 150B, 150C, 150D for matching with the apertures 140A, 140B, 140C, 140D of the second half 130B of the separation unit 102.

Figure 7B:
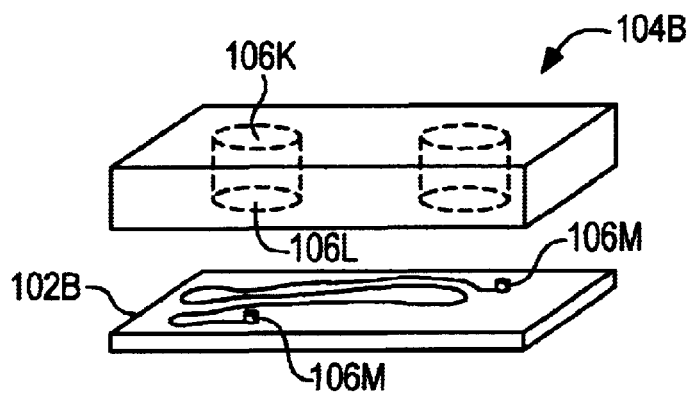
FIG. 7B shows an exploded isometric view of an embodiment of an reservoir unit being coupled to a separation unit according to the present invention.

Alternatively, as shown in FIG. 7B, the reservoir unit 104B can be made such that the reservoirs (e.g., 106K) have a bottom (e.g., 106L), which is thin so that it can be punctured by a protrusion arm 106M from the separation unit 102B. The protrusion arms 106M each can have a channel for allowing fluid to flow from the reservoir into the separation unit 102B. It is preferred that the reservoir unit 104 is made of a material that can seal against the separation unit 102B well to prevent leakage.

Figure 7C:
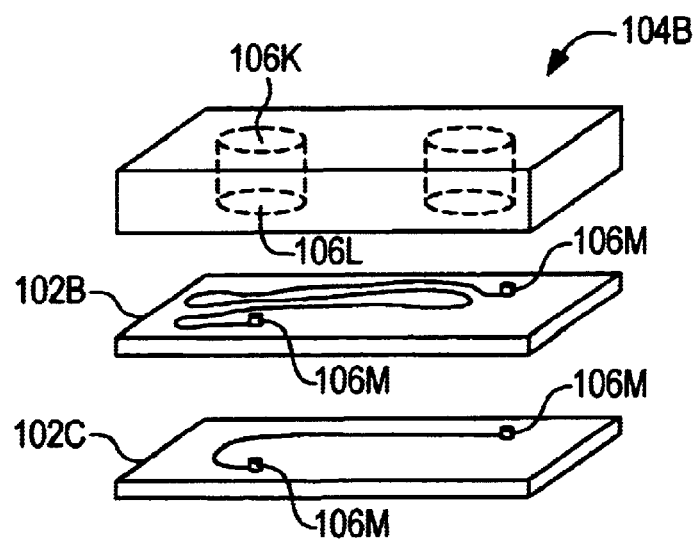
FIG. 7C shows an exploded isometric view of an embodiment of a reservoir unit capable of being coupled to two separation units in succession according to the invention.

FIG. 7C depicts the same device as FIG. 7B except that an additional separation unit 102C is employed. Thus, the reservoir unit 104B can be made such that the reservoirs (e.g., 106K) have a bottom (e.g., 106L), which is thin so that it can be punctured by a protrusion arm 106M from the separation units 102B or 102C in succession. As shown, separation units 102B and 102C have channels of different lengths.

As mentioned previously, the upper side of the reservoir unit 104 is in contact with a membrane 108, which functions to seal the prepackaged liquid from escaping from the reservoir unit 104 before being used for analysis. This membrane 108 can be applied and affixed to the reservoir unit to prevent liquid escaping when the reservoir unit is being manufactured. The membrane 108, like the cover sheet on the underside of the reservoir unit 104, can be made with polymeric material, or even paper, as long as the paper membrane is coated with an appropriate substance to protect from disintegration when wet.

The power unit 110 has probes 112A, 112B, 112C, 112D for puncturing through the membrane 108 to provide energy to drive the liquid or chemical analytes through the microchannel. One source of energy is pressure. A probe can be hollow and connected to a pressure source such as a pump for driving liquid through the microchannel, as in the case of LC. Another energy source is electricity. For example, in CE, two probes can be connected to a electrical power supply to provide a voltage difference to drive electrolytes and analytes through the microchannel due to the electrical characteristics of the electrolytes and analytes.

The support plate 118 provides support for the separation unit in the apparatus so that the modular coupling of the parts of the apparatus 100 is secure and free of leaks. A hole 152 provides access for the detection device 126 to the underside of the separation unit 102 (i.e., access of an optical fiber 128B). The detection device's other optical fiber 128A faces the microchannel 132 from the upper side of the separation unit 102. One of these optical fibers, e.g., optical fiber 128A, can be the light source and the other optical fiber, e.g., optical fiber 128B, can be the light collector, the signal of which is transferred to a processor to be analyzed. As stated earlier, preferably, the support plate is made of a thermally conductive material to facilitate uniform heat distribution and control in the separation unit 102.

The peltier device 120 can be used to heat or cool the support plate 118 directly, and the separation unit indirectly. The peltier device has the characteristic of presenting a heating upper surface to the support plate while presenting a cooling lower surface to the heat exchanger when electrical currently is applied in one direction and, in the reverse, presenting a cooling upper surface and heating lower surface while electricity is applied in the opposite direction. The heat exchanger 124 that is modularly coupled to the underside of the Peltier device 120 has a flat surface for providing good thermal contact with the support 118. The heat exchanger 124 further has fins 156 on its underside for dissipation of heat from the underside of the Peltier device or for absorbing heat from the environment when the underside of the Peltier device is cold. It is to be understood that the Peltier device 120 may not be needed if the temperature of the separation unit 102 can be kept relatively close to the desired temperature with only the heat exchanger, or even without the heat exchanger.

Further, other types of temperature control devices, besides Peltier device, can be used to control the temperature of the separation unit. Examples of suitable cooling devices include cooling or heating by circulating air or a liquid.

Making the Modularly Coupled Apparatus

The separation unit of the present invention are similar to the planar column devices described in the patents of Kaltenbach et al., Witt et al., and Swedberg et al. above and can be made by methods described therein. Briefly stated, they can be made by forming (or micromachining) microstructures such as microchannels and depressions, as well as holes, or even electrical components, such as electrodes, antennas, and electrical connectors, on a substrate and later arranging a cover member (or cover plate half) on the substrate to form a separation unit. As stated previously, the cover plate half can be a cover plate which, in conjunction with a microchannel of the substrate, defines the separation microchannel or compartment. The cover member can also be another substrate piece with microstructures with or without components so that the two substrate pieces act as two structurally similar halves that form a body when becoming attached in alignment. The microchannels of the two halves can define the separation compartment.

Figure 8:
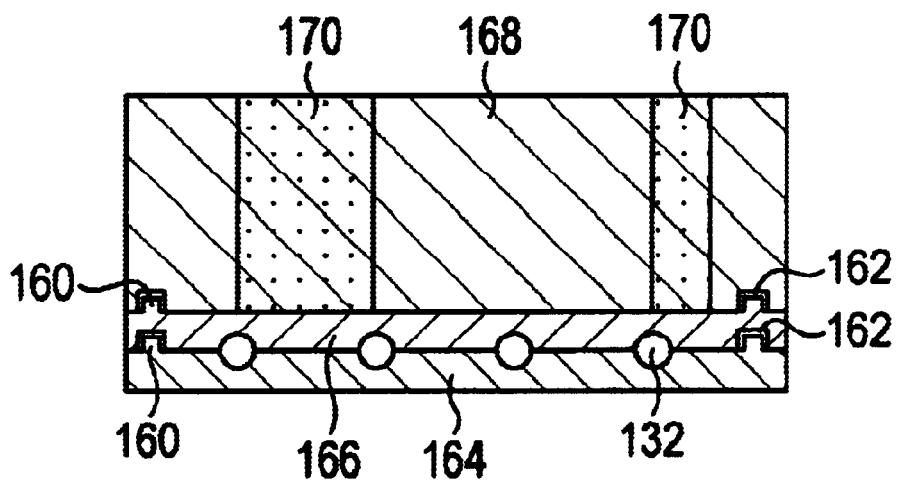
FIG. 8 shows a sectional view of an embodiment having protrusions and receptacles to them for alignment of components according to the present invention.

In yet another alternative, the separation unit can have only one piece (i.e., one half) that has microchannel(s). This one-piece separation unit can be coupled directly to the reservoir unit (as if it is another half). By directly coupling the reservoir unit (e.g., by peeling off a membrane on the bottom of the reservoir unit to allow liquid to reach the microchannel(s) on the one-piece separation unit) the resulting device is very compact. To facilitate the alignment of different pieces of the device, such as the alignment of halves of the separation unit and alignment of modularly coupled units (e.g., the separation unit with the reservoir unit), matching microstructures such as tongues and grooves, mating protrusions and notches that match on the two halves or on the modular units (which can be the separation unit and the reservoir unit) can be included. FIG. 8 shows examples of such matching microstructures: protrusions 160 that fit into receptacles 162 to anchor the first half 164 to second half 166, as well to anchor the second half 166 to the reservoir unit 168, which has reservoirs 170. The two halves 164 and 166 form the separation unit, which has a microchannel 132.

Microstructures such as microchannels, tongues and grooves, etc., can be formed on the substrate by techniques such as etching, laser ablation, and the like. The substrate can be processed (e.g., by laser ablation or etching) to obtain the microstructures. Suitable substrates include, for example, polymers, glass, silicon, silicon dioxide, quartz, ceramics, and the like. The part of the separation unit at which the detection device detects light signal from the microchannel should be made of a material that is at least translucent, preferably transparent, to the light used for detection.

After the halves of a separation unit are formed, for example, after constructing the microchannels by laser-ablation on polyimide substrates, the two (or more than two) halves are then bonded together so that the microchannels of adjacent halves face and unite with each other to form a separation microchannel (or separation compartment). As stated above, a variety of techniques can be used to form (or micromachine) microstructures (e.g., microchannels and holes), as well as larger structures (e.g., chambers and reservoirs) on the body of the miniaturized column device of the present invention. Such techniques include, but are not limited to, dry etching, chemical etching, LIGA, and laser ablation. Depending on the techniques selected, the appropriate microstructures can be formed in a suitable substrate either before or after the formation of the necessary electrical components on the substrate.

In the practice of the present invention, a preferred substrate comprises a polyimide material such as those available under the trademarks KAPTON or UPILEX from DuPont (Wilmington, Del.), although the particular substrate selected may comprise any other suitable polymer or ceramic substrate. Polymer materials particularly contemplated herein include materials selected from the following classes: polyimide, polycarbonate, polyester, polyamide, polyether, polyolefin, or mixtures thereof.

Further, the polymer material selected may be produced in long strips on a reel, and, optional sprocket holes along the sides of the material may be provided to accurately and securely transport the substrate through a step-and-repeat process. the selected polymer material can be transported to a laser processing chamber and laser-ablated in a pattern defined by one or more masks using laser radiation. Although the microchannel has been represented in a generally extended form in the figures, microchannels formed under the invention may be in a large variety of configurations, such as in a straight, serpentine, spiral, or any tortuous path desired. Further, the microchannel may be formed in a wide variety of channel geometries including semi-circular, rectangular, rhomboid, and the like, and the channels may be formed in a wide range of aspect ratios. It is also noted that a device having a plurality of microchannels formed thereon is within the scope of the present invention.

The use of substrates such as polyimides in the construction of miniaturized columns under the invention allows the possibility of using refractive-index (RI) detection to detect separated analytes of interest passing through the subject columns. In this regard, the provision of an associated laser diode which emits radiation at a wavelength where polyimide is "transparent" (such as at >450 nm) allows for the detection of analytes passing through the microchannel, for example, by conducting the light through optical fibers such as optical fibers 128A, 128B in FIG. 1. In addition, electrodes (not shown), electrical conductors may be formed in the halves such as 130A, 130B to provide connection to electrical power. Methods for laying such electrically conducting materials in small devices are known in the art.

The reservoir unit, e.g., reservoir unit 104 can be made in a wide variety of techniques in a wide variety of materials, including laser ablation, chemical etching, and tradition machining techniques, because the dimensions of the reservoirs are significantly larger than the microchannels. Preferably, for making the reservoir unit, a material that is a little soft and resilient, e.g., polymeric such as rubber, silicone, butyl rubber, and polytetrafluoroethylene, can be used to prevent leaks, so long as the material is chemically compatible with the liquid contained in the reservoirs. Another suitable material is PDMS (polydimethylsiloxane). Furthermore, the reservoir unit can be made with a harder material, such as a hard polymeric material (e.g., polyvinylchloride, polystyrene) and coated with a softer, elastic layer for sealing against the separation unit.

The membrane 108 is made of a material that can seal the reservoir unit and the power unit against fluid leakage. The power unit 110 can be made with a wide variety of materials and dimensions, so long as it can support the probes firmly. Proper connections are provided on the power unit to supply power source, such as electricity, hydraulic pressure, and the like. The probes, such as probes 112A, 112B, 112C, 112D of FIG. 1 are made of materials adequately stiff for puncturing through the membrane 108. If a probe is used for conducting electricity, it should be made of an electrically conducting material, such as a suitable metal. The tips of the probes are preferably sharp to puncture the membrane covering the reservoir unit cleanly. The probes should also be compatible with the liquid with which it will contact. Material and construction of support plates, peltier devices and heat exchangers are known in the art.

The various parts (or components, or pieces) of the modularly couplable apparatus of the present invention are assembled together to form the analytical apparatus, for example, that shown in FIG. 2. Preferably, there are notches, tongue and groove structures, and the like, in the various parts to facilitate efficient alignment for coupling. The parts are held together in adequately tight manner, for example, by means of clamps, springs, clips, screws, nuts and bolts, and the like, to prevent liquid leakage. Samples containing analyte or analytes can be introduced into the apparatus and power can be supplied to drive the analyte or analytes of interest through the microchannel. Methods of driving liquid and analytes, as well as methods of detection of analytes in microchannels are known in the art and can be adapted for application in the present modular apparatus.

The present modularly coupled analytical apparatuses can be used to analyze a wide variety of chemical, biochemical, and biological samples. The physics, and chemistry of such applications are known in the art.

Although the preferred embodiment of the present invention has been described and illustrated in detail, it is to be understood that a person skilled in the art can make modifications within the scope of the invention. For example, additional layers of material can be interposed between the parts described in the aforementioned apparatuses. Another example is that the support plate, peltier device, as well as the heat exchanger can be replaced with an exchanger that has a surface suitable for coupling with and supporting the separation unit so long as the heat exchanger can maintain a suitable temperature on the separation unit.

What is claimed is:

1. A modular microchannel apparatus for the chemical analysis of an analyte in a sample, comprising:
   (a) a plurality of separation units each effective to carry out a different analytical application of interest and comprised of a first solid substrate having a microchannel present in a surface thereof, wherein the microchannel in each separation unit is of a different length corresponding to the analytical application of interest for the separation unit containing the microchannel and forms a separation column or capillary that separates the analyte from the sample according to the molecular characteristics of the analyte;
   (b) a single reservoir unit in the form of a plate comprised of a reservoir that contains a liquid for introduction into each of the microchannels of the separation units in succession; and
   (c) an external power source capable of generating an electric field difference between electrically conductive probes extending into the reservoir unit, the power source operatively connected to the reservoir unit for electrokinetically driving the liquid from the reservoir through the microchannels of the separation units,
   wherein the reservoir unit has dimensions that enable the operative and modular coupling of the reservoir unit to each separation unit in succession to allow liquid from the reservoir to be electrokinetically driven, by a power-source-generated electric field difference between the probes, into the microchannel of the separation unit that is operatively and modularly coupled to the reservoir unit, and
   at least one of the separation units is chip-shaped and further comprised of a second substrate having a surface facing and joining the first substrate surface, thereby forming the microchannel.

2. An apparatus according to claim 1, wherein the first and second substrates serve as first and second halves, respectively, of the at least one separation unit, and the facing and joining substrate surfaces are substantially planar.

3. An apparatus according to claim 1, wherein at least one of the separation units has one or more openings leading to the microchannel capable of admitting liquid reagents such that when the separation unit and the reservoir unit are operatively and modularly coupled, the openings are aligned with the reservoirs thereby allowing the liquid reagents and the analyte to pass from the reservoirs into the microchannel without substantial leakage.

4. An apparatus according to claim 2, wherein at least one of the separation units includes a substrate comprised of a material other than silicon or silicon dioxide in which the first microchannel is formed by laser ablation.

5. An apparatus according to claim 2, wherein the reservoir unit includes a membrane that covers at least one of the reservoirs confining the prepackaged liquid reagent therein, wherein the membrane is penetrable with a probe for applying a driving force to drive movement of liquid reagent and analyte from the reservoir through the microchannel of at least one of the separation units.

6. An apparatus according to claim 2, wherein both substantially planar surfaces of the separation unit having a first half and a second half have a laser-ablated channel thereon and the two channels join to form the microchannel.

7. An apparatus according to claim 2, wherein the channel of at least one separation unit is formed by laser ablation.

8. An apparatus according to claim 2, wherein the external power unit comprises a powering plate operatively and modularly coupled to the reservoir unit, the powering plate having an electrical connection to the reservoir to provide a driving force to drive movement of the liquid reagents and analyte from the reservoir through the microchannel.

9. The apparatus according to claim 2, further comprising a support plate for operatively and modularly coupling to the separation units.

10. An apparatus according to claim 9, further comprising a peltier plate operatively and modularly coupled to the support plate for controlling the temperature of at least one of the separation units.

11. An apparatus according of claim 10, wherein the pettier plate can be used to heat or cool at least one of the separation units by selecting an appropriate mode of operation.

12. An apparatus according to claim 11, further comprising a heat exchanger operatively connected to the peltier plate to transfer heat between the peltier plate and the surrounding environment.

13. A kit for making a modular microchannel apparatus for the chemical analysis of an analyte in a sample, comprising:
   (a) a plurality of separation units each effective to carry out a different analytical application of interest and comprised of a first solid substrate having a microchannel present in a surface thereof, wherein the microchannel in each separation unit is of a different length corresponding to the analytical application of interest for the separation unit containing the microchannel and forms a separation column or capillary that separates the analyte from the sample according to the molecular characteristics of the analyte;
   (b) a single reservoir unit in the form of a plate comprised of a reservoir that contains a liquid for introduction into each of the microchannels of the separation units in succession; and
   (c) an external power source capable of generating an electric field difference between electrically conductive probes and having dimensions that enable its modular and operative connection to the reservoir unit for electrokinetically driving the liquid from the reservoir through the microchannels of the separation units,
   wherein the reservoir unit has dimensions that enable the operative and modular coupling of the reservoir unit to each separation unit in succession, the probes extend into the reservoir unit when the reservoir unit is operatively coupled to the external power source, a power-source-generated electric field difference between the probes electrokinetically drives liquid from the reservoir into the microchannel of the separation unit that is operatively and modularly coupled to the reservoir unit, and at least one of the separation units is chip-shaped and further comprised of a second substrate having a surface facing and joining the first substrate surface, thereby forming the microchannel.

14. A modular microdevice for analyte analysis, comprising:

(a) a plurality of separation units each effective to carry out a different analytical application of interest and comprised of a solid substrate having a micro channel present in a surface thereof, wherein the microchannel in each separation unit is of a different length corresponding to the analytical application of interest for the separation unit containing the microchannel and forms a separation column or capillary that separates an analyte from a sample according to the molecular characteristics of the analyte;

(b) a single reservoir unit in the form of a plate comprised of a plurality of reservoirs, wherein each reservoir contains a liquid, each liquid is suitable for introduction into a microchannel of a separation unit; and (c) an external power source capable of generating an electric field difference between electrically conductive probes extending into the reservoir unit, the power source operatively connected to the reservoir unit for electrokinetically driving liquids from the reservoir unit through the microchannels of the separation units, wherein the reservoir unit has dimensions that enable the operative and modular coupling of the reservoir unit to each separation unit in succession to allow liquid from at least one of the plurality of reservoirs to be electrokinetically driven, by a power-source-generated electric field difference between the probes, into the microchannel of the separation unit that is operatively and modularly coupled to the reservoir unit, and at least one of the separation units is chip-shaped and further comprised of a second substrate having a surface facing and joining the first substrate surface, thereby forming the microchannel.

15. The modular microchannel apparatus system of claim 14, wherein each of two separation units of the plurality has a microchannel of a different size.

* * * * *